(12) United States Patent
Huang

(10) Patent No.: US 10,889,608 B2
(45) Date of Patent: Jan. 12, 2021

(54) ESTER OF AMINOGLYCAN AND USES THEREOF

(71) Applicant: Chengdu Auli Ecological Technology Development Co., Ltd., Sichuan (CN)

(72) Inventor: Yong Huang, Chengdu (CN)

(73) Assignee: CHENGDU AULI ECOLOGICAL TECHNOLOGY DEVELOPMENT CO., LTD., Chengdu (CN)

( * ) Notice: Subject to any disclaimer, the term of this patent is extended or adjusted under 35 U.S.C. 154(b) by 218 days.

(21) Appl. No.: 16/068,073

(22) PCT Filed: Jan. 4, 2017

(86) PCT No.: PCT/CN2017/070181
§ 371 (c)(1),
(2) Date: Jul. 3, 2018

(87) PCT Pub. No.: WO2017/118389
PCT Pub. Date: Jul. 13, 2017

(65) Prior Publication Data
US 2020/0283464 A1    Sep. 10, 2020

(30) Foreign Application Priority Data

Jan. 4, 2016  (CN) .......................... 2016 1 0000669
Jan. 15, 2016 (CN) .......................... 2016 1 0025970

(51) Int. Cl.
| | | |
|---|---|---|
| *A01N 43/04* | (2006.01) | |
| *A61K 31/70* | (2006.01) | |
| *C07H 13/10* | (2006.01) | |
| *A01N 57/32* | (2006.01) | |
| *A61P 31/12* | (2006.01) | |

(52) U.S. Cl.
CPC ............. *C07H 13/10* (2013.01); *A01N 57/32* (2013.01); *A61P 31/12* (2018.01)

(58) Field of Classification Search
None
See application file for complete search history.

(56) References Cited

FOREIGN PATENT DOCUMENTS

| CN | 104311683 A | 1/2015 |
|---|---|---|
| CN | 104430346 A | 3/2015 |
| CN | 104510729 A | 4/2015 |
| CN | 104784199 A | 7/2015 |

OTHER PUBLICATIONS

Wang et al. Carbohydrate Research (2014), vol. 386, pp. 48-56.*

* cited by examiner

*Primary Examiner* — Patrick T Lewis
(74) *Attorney, Agent, or Firm* — Volpe Koenig

(57) ABSTRACT

A new biomaterial is disclosed. The biomaterial is prepared by mixing glycosaminoglycan with a phosphoric acid, phosphate ester, or salt or derivative thereof under the action of a catalyst in a liquid reaction medium at a pH of 2.1 to 4.9. The obtained material is capable of enhancing the immunological resistance in human and in animals, treating diseases in human and in animals caused by viruses or bacteria, strengthening the anti-stress ability of animals, improving the appetite of animals, promoting the growth of animals, inhibiting the growth of tumor, lowering blood fat level, as well as preventing and treating viral diseases in plants.

3 Claims, No Drawings

ESTER OF AMINOGLYCAN AND USES THEREOF

CROSS REFERENCE TO RELATED APPLICATIONS

This application is a 35 USC § 371 national stage application of PCT/CN2017/070181, which was filed Jan. 4, 2017 and claimed priority to CN 201610000669.X, filed Jan. 4, 2016, and CN 201610025970.6, filed Jan. 15, 2016, all of which are incorporated herein by reference as if fully set forth.

FIELD OF THE INVENTION

The present invention belongs to the biotechnological field. It is related to enhance the immune resistance in human bodies and in animals through feeding or drinking, resulting from a novel ester of aminoglycan and uses thereof.

BACKGROUND OF THE INVENTION

With the continuous progress of social civilization, people are more aware of the impact of environmental toxins on human health. The immune capability is declined due to fast pace of modern life, work pressure and insufficient sleep as well as the substances from air and drinking water and food that may damage the living cells. This has resulted in harmful impact and exposed the human body to the pathogen infection. In the meantime, the extensive use of antibiotics and drugs may lead to the severe development of pathogen resistance via variation that makes it even more difficult to be killed by the drugs such as the avian influenza virus as an example. The extensive study has discovered that human health can be protected if the cells are supplemented with the essential nutrients on time. This helps the cells resist the erosion from the harmful substances and pathogen infection, thus promote health in human bodies.

In the livestock husbandry, the extensive use of hormones or antibiotics promotes the growth of livestock but reduces their immune capability against the stress. The weakened immune resistance may give way to the disease prevalence and result in the mass mortality of the livestock. The stress can inhibit the excitability of the central nerve for feeding and cause dyscrasia of neuroendocrine and parasecretion of hormone such as thyroxines and adrenalines. For example, the following aspects in the swine husbandry have been observed when the immune resistance is low against stress. 1) The growth rate is declined with less food intake and slower weight gain of the pigs. 2) The reproduction is hindered because the ovarian function of sow is subsided with the pregnancy rate reduced and the abortion and stillbirth increased. The yield of sow lactation and rate of piglet survival are decreased. The boar represents lower libido and poor semen quality with less number of sperm and lower vitality accompanied by an increased deformity rate. 3) The dermatitis nephrotic syndrome and dysentery of piglets and indefinable high fever and chronic ileitis and other diseases are increased. 4) Overall the pork quality is rather poor. 5) When the immune resistance is low the infectious diseases are increased in the aquaculture too. This has caused the disease prevalent and mass mortality. The shrimps and crabs grow slowly and are easy to suffer from difficulty in shucking.

The traditional method to enhance the immune resistance against stress in livestock is to feed the livestock with fats, synthetic amino acids, electrolytes, minerals, vitamins and organic acids, or antibiotics and vaccines. This has achieved certain effect. However, due to the extensive use of these products particularly the antibiotics the food safety is becoming an important issue due to residues. Furthermore, the increasing resistance from the pathogens is concerned because this has posed serious challenges to the human health and to the livestock.

In recent years, the experts in the world have paid attention to the role of polysaccharides in improving the immune resistance in human body and in livestock. A number of researches in laboratory in the world has disclosed that polysaccharides such as chitosan are able to enhance the anti-stress immunity of the animals when used as feed additives. However, the application of these polysaccharides is unstable in practice. The major problem is that these polysaccharides cannot provide a satisfied effect on protection to the livestock when the animals are already under stress or sick.

SUMMARY OF THE INVENTION

The points and values disclosed in the present invention are not limited to the exact ranges or values represented. For numeric ranges, the end points of the ranges, the end points of the ranges and the discrete point values, and the discrete point values may be combined to obtain one or more new numeric ranges, which shall be deemed as having been disclosed specifically in this document.

In order to overcome the deficiencies of the prior art, compared with the reported polysaccharide, the preparation containing ester of aminoglycan in this invention is made from the aminoglycans and phosphoric acids, phosphate esters or salts or its derivatives under the action of catalysts (especially metal salts or microorganisms). The invented product can significantly activate the cellular immune function of human bodies and animals, thereby enhancing the immunity of human bodies and animals and achieving the effects of treating human and animal diseases caused by viruses and bacteria. It is beneficial on inhibiting tumor, It can prevent plant diseases as well.

The ester of aminoglycan provided by the present invention comprises at least one of the following structural units:

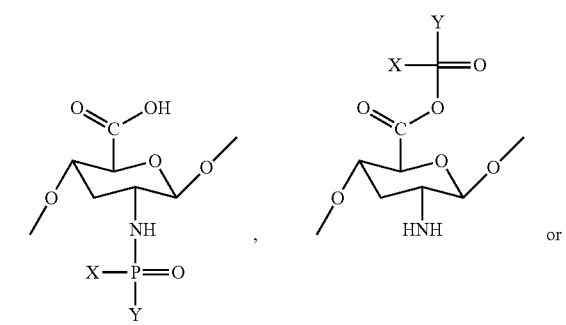

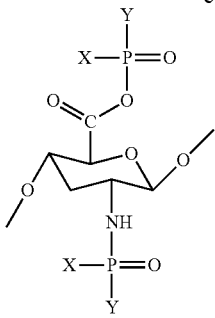

wherein X is —OH, —O—CH$_2$—CH$_2$—N—(CH$_3$)$_3$, —O—CH$_2$—CH$_2$—NH$_2$, metal element or non-metal element independently; and Y is —OH independently,

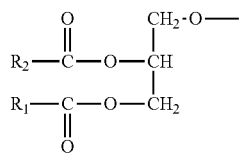

(e.g., R$_1$ and R$_2$ may be —CH$_3$ independently),

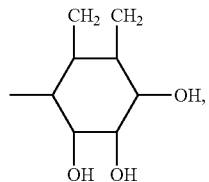

metal element or non-metal element. According to a preferred embodiment of the present invention, the ester of aminoglycan is a deacetylated chitin modified by group

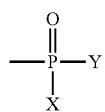

(i.e., the ester of aminoglycan possesses a skeleton structure of deacetylated chitin).

The ester of aminoglycan provided by the present invention can be prepared from aminoglycans and phosphoric acids, phosphate esters, or salts or derivatives under the action of catalysts, in a liquid reaction medium with pH between 2.1 and 4.9. In order to obtain ester of aminoglycan with higher purity, ethanol precipitation may further be performed. The function of new materials prepared from aminoglycans and phosphoric acids, phosphate esters, or salts or derivatives thereof under the action of catalysts includes but is not limited to activate the cellular immune functions in human bodies and animals, thereby to improve the immune resistance in human bodies and animals, to cure human and animal illness caused by viruses and bacteria, to benefit on inhibiting tumor, and to prevent plant diseases especially mosaic virus as well.

The aminoglycans employed for the ester of aminoglycan may be polymerized from 2 to 7000 amino-containing monosaccharides. The basic molecular formula that constitutes these glycans is an amino-containing monosaccharide having 6 carbon atoms, which may come from plants, animals or microorganisms, including but not limited to aminopolysaccharides, amino oligosaccharides, deacetylated chitins, glycosaminoglycans, chitosans, astragalus polysaccharides, *ginseng* polysaccharides, *panax notoginseng* polysaccharides, chu-sheng polysaccharides, *ganoderma* polysaccharides, lentinan polysaccharides, zymosan, etc. Most preferably, the aminoglycan is the deacetylated chitin.

Preferably, the phosphoric acids, phosphate esters, or salts or derivatives thereof used for the ester of aminoglycan include but are not limited to sodium phosphate, sodium hydrogen phosphate, potassium phosphate, potassium hydrogen phosphate, phosphatidyl ethanolamine, phosphatidylcholine, phosphatidylserine, phosphatidylinositol, phosphatidylglycerol, diphosphatidylglycerol, phosphatidic acid, lecithin, etc., and most preferably lecithin.

In the present invention, the catalysts may include but are not limited to metal salts and/or microorganisms. Preferably, the catalysts include but are not limited to at least one of calcium chloride, sodium chloride, potassium chloride, zinc oxide, calcium oxide, calcium superphosphate, sodium tripolyphosphate, sodium hydrogen carbonate, disodium hydrogen phosphates, sodium polyphosphates, potassium dihydrogen phosphate, dipotassium hydrogen phosphate, sodium sulfate, zinc sulfate, copper sulfate, zinc acetate, potassium sulfate, calcium carbonate, calcium amino acid, zinc amino acid, calcium dextran, zinc dextran, sodium carbonate, calcium bicarbonate, potassium bicarbonate, calcium sulfate, calcium nitrate, calcium gluconate, potassium carbonate, and bio-enzyme. More preferably, the catalysts are hydrophosphates (e.g., disodium hydrogen phosphates and/or potassium dihydrogen phosphates) and/or fermentation products of *Trichoderma* (such as *Trichoderma harzianum*). The fermentation product refers to a product obtained by inoculating the microorganisms (i.e., *Trichoderma*, such as *Trichoderma harzianum*) to a culture medium and conducting fermentation.

The raw materials used above are all commercially available.

The preparation containing ester of aminoglycan provided by the present invention is obtained by the following step: incubating aminoglycans and phosphate esters, or salts or derivatives thereof at a pH range from 2.1 to 4.9 in the presence of fermentation products of *Trichoderma* and hydrophosphates, and then performing a solid-liquid separation. According to the preferred embodiment of the present invention, the aminoglycan is deacetylated chitin, the phosphate ester or salt or derivative thereof is lecithin, and the *Trichoderma* is *Trichoderma harzianum*, the hydrophosphate is disodium hydrogen phosphate and/or potassium dihydrogen phosphate, and the weight ratio of the aminoglycans, phosphateesters or salts or derivatives thereof, and hydrophosphates is 1.5-3:0.8-1.5:0.8-1 (preferably 2:1:1). The incubating condition may include temperature ranging from 25 to 30° C., and time ranging from 70 to 80 h. After solid-liquid separation, the preparation may further be precipitated with absolute ethanol (solid contents are collected) to obtain ester of aminoglycan with higher purity.

The present invention further provides an use of the above-mentioned ester of aminoglycan or preparation containing ester of aminoglycan in enhancing the immune resistance in human and in animal, treating diseases in human and animals caused by viruses or bacteria, strengthening the anti-stress ability of animals, improving the appetite of animals, promoting the growth of animals, inhibiting the growth of tumor, reducing blood lipid level and preventing and controlling viral diseases of plants, and particularly provides an use of the same in preparing drugs for enhancing the immune resistance in human and in animals, treating diseases in human and animals caused by viruses or bacteria, strengthening the anti-stress ability of animals, increasing the appetite of animals, promoting the growth of animals, inhibiting the growth of tumor, reducing blood lipid level and preventing and controlling viral diseases of plants.

In the present invention, the diseases in human or animals mentioned include but are not limited to diseases harmful to human health, such as diseases caused by viruses which include but not limited to influenza virus, hepatitis A virus, hepatitis B virus, hepatitis C virus, HIV, and herpes virus; cancerous diseases caused by cellular canceration; as well as diseases harmful to animals, including but not limited to viral and bacterial diseases harmful to livestock, poultry as well as aquatic product of fish, shrimp and crab, such as avian influenza, swine influenza, picornvirus disease (蛙环爪病), saprolegniasis and streptococcusis.

The technical problem solved by the present invention is the new biological material prepared by catalyzing aminoglycans and phosphates or derivatives thereof in a liquid reaction medium with a pH from 2.1 to 4.9, which can be used to inhibit the growth of tumor, reduce blood lipid level, enhance the immune resistance of human and animals, treat diseases in human and animals caused by viruses or bacteria, strengthen the anti-stress ability of animals, improve the appetite of animals, promote the growth of animals and prevent and control diseases in plants.

The first innovation of the present invention is the ester of aminoglycan prepared by reacting polysaccharides polymerized by 2 to 7000 amino-containing monosaccharides with one or more of phosphoric acids or phosphate esters or salts or derivatives thereof. The second innovation is that this reaction is completed in the liquid medium with a pH between 2.1 and 4.9. In the third innovation, the ester of aminoglycan of the present invention has effects on significantly activating the cellular immune function in human and in animals, improving the immunity in human and in animals, thereby treating diseases in human and in animals caused by viruses and bacteria, in the same time, it has effects on inhibiting tumors and preventing and controlling viral diseases of plants.

EMBODIMENTS

The present invention makes further description based on the following examples. Those skilled in the art know that the following examples merely illustrate the present invention. On the premise of not departing from the spirit of the invention, any improvements and substitutions made to the invention are within the protection scope of the invention.

Example 1

Preparing the preparation containing ester of aminoglycan of the present invention.

The liquid fermentation medium is prepared with soluble starch 25 g, calcium carbonate 5 g, potassium dihydrogen phosphate 2 g and ammonium sulfate 5 g are mixed in 1000 mL water, then add 4.0 mL corn oil and mix well without adjusting the pH. The medium is sterilized at 121° C. for 20 min. The spores of purified *Trichoderma harzianum* (purchased from Chengdu Tepu Bio-Tech Co., Ltd.) are collected from a test tube containing sterile water using an inoculation loop. The spores are dispersed from hyphae and filtered through a sterile gauze to remove hyphae. After the spore concentration is adjusted to $10^7$ cfu/mL the spores are inoculated to the liquid fermentation medium in an inoculum size of 1%. After cultured at 28° C. and 150 r/min for 48 hours, 10 g sterilized deacetylated chitins (purchased from Sigma-Aldrich Company) and 5 g lecithin (purchased from Sigma-Aldrich Company) and 5 g of disodium hydrogen phosphate are added. The culture is further incubated at 28° C. and 150 r/min for 72 hours. The culture is filtered to collect the solution that is precipitated with 2-3 times of absolute ethanol. Carry out a suction filtration and the precipitates are diluted in water to make a microemulsion of ester of aminoglycan. The microemulsion is further adjusted to achieve the content of ester of aminoglycan at 0.01 mg ml. Upon detection, the microemulsion of ester of aminoglycan obtained in this example has an ester of aminoglycan which comprises the following structural unit,

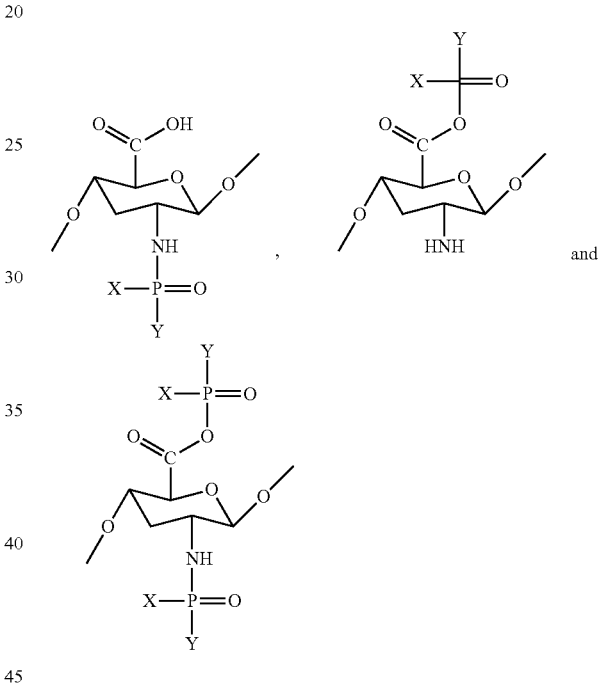

(wherein X is —O—$CH_2$—$CH_2$—N—$(CH_3)_3$, and Y is

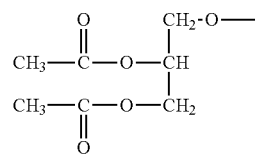

).

Example 2

Enhanced immune resistance effect of the preparation containing ester of aminoglycan of the present invention.

*Macaca fascicularis* (Yunnan Primate Laboratory Animal Co., Ltd.) are managed according to the country standard Feeding and Management and Operating Guideline for Experimental Animals. Fifteen *Macaca fascicularis* are divided into 3 groups with each group of 5 *Macaca fascicularis*. The group A is given sterile water as control. The group B is given the ester of aminoglycan obtained in Example 1 at a rate of 3 mg/3 ml/kg. The group C is given the ester of aminoglycan obtained in Example 1 at a rate of 9 mg/3 ml/kg. The administration to the animals is carried out at 10:00 am (±30 min). The drug and dose given in each group are shown in the table below:

TABLE 1

| Arrangement of the Test Groups | | |
|---|---|---|
| Group | Treatment | Dose (dose/water/body weight) |
| Group A | Sterile water | 0 mg/3 ml/kg |
| Group B | Ester of aminoglycan | 3 mg/3 ml/kg |
| Group C | Ester of aminoglycan | 9 mg/3 ml/kg |

The detection in the antibody demonstrated that immunoglobulins IgG and IgM in blood increased significantly in Groups B and C that were orally given the ester of aminoglycan obtained in Example 1, especially, the ester of aminoglycan had a significant effect on increase of IgM. After 4 weeks under the administration, the level of IgM reached the maximum in both Group B and Group C that is 17% and 28% higher than that in Group A (control group), respectively.

Immunocytokine assays also demonstrated that the new material ester of aminoglycan from the present invention significantly improved the level of cytokines IL10 and TNF-a in blood (Table 2). The increase of the level was related to the rate of the ester of aminoglycan concentration.

TABLE 2

| Effect of ester of aminoglycan on immunocytokines level | | | | | | |
|---|---|---|---|---|---|---|
| | IL-10 (pg/ml) | | | TNF-a (pg/ml) | | |
| Treatment | The 9$t^h$ day | The 15$^{th}$ day | The 30$^{th}$ day | The 9$^{th}$ day | The 15$^{th}$ day | The 30$^{th}$ day |
| Group A | 31.40 | 189.34 | 74.85 | 560.52 | 1057.46 | 592.20 |
| Group B | 145.61 | 181.16 | 118.08 | 250.63 | 1366.14 | 1037.07 |
| Group C | 146.55 | 805.80 | 536.43 | 830.60 | 1587.15 | 1730.95 |

Example 3

Effect on treating swine viral illness by the preparation containing ester of aminoglycan of the present invention.

Twenty pigs with symptom of hog cholera were selected in a hog farm. They were divided into treatment group by ester of aminoglycan and control group without treatment. Two groups of ill pigs was consistent in age, clinical manifestation and degree of illness. There were 10 pigs in treatment with the ester of aminoglycan and 10 in control respectively. The ester of aminoglycan was added in the feeding materials uniformly based on a dose of 3 mg per kg body weight in treatment. The control group is separated from the treatment and received the conventional management. The mental status, body temperature and food intake of the pigs were observed every day. Five days after the test started, the ill pigs fully recovered from body temperature and appetite and mental status and all clinic symptoms disappeared were recorded as cured. The ill pigs partially recovered from body temperature and appetite and mental status were recorded as improved. Both improvement and cure were regarded to be effective. Those with inactivity, anorexia or even death after 10 days from the test were recorded to be ineffective.

TABLE 3

| Effect of ester of aminoglycan on treating viral disease of swine | | | | | | | | |
|---|---|---|---|---|---|---|---|---|
| | | Cured | | Improved | | Effective | | Ineffective |
| Groups | Number of cases | Number of swine | Cured Rate % | Number of swine | Improved Rate % | Number of swine | Effective Rate % | Number of swine | Ineffective Rate % |
| Control group | 10 | 0 | 0 | 1 | 10 | 1 | 10 | 9 | 90 |
| Aminoglycan ester group | 10 | 8 | 80 | 7 | 20 | 10 | 100 | 0 | 0 |

By adding ester of aminoglycan into the feeding materials, 8 ill pigs were cured, 2 ill pigs were improved. In the control group received the conventional treatment, 5 pigs died and only 1 pig was improved. This demonstrated that the ester of aminoglycan had a significant effect on the treatment of viral diseases in pigs. It was proved that the ester of aminoglycan from the present invention had a remarkable feature of simplicity in operation and excellent effect compared with the conventional management in which antibiotic drugs were injected.

Example 4

The effect of the preparation containing ester of aminoglycan from the present invention on the prevention and control of plant virus diseases.

The ester of aminoglycan prepared in Example 1 was used to prevent and control mosaic virus disease in *Capsicum annum*. *Capsicum annuum* which had viral symptom was selected for this test. The test were arranged as 5 treatments. Each treatment was designed with 4 blocks with 50 plants in each block. Treatment 1 was a dilution of the ester of aminoglycan at 1000 times. Treatment 2 was a dilution of the ester of aminoglycan at 500 times. Treatment 3 was a dilution of the ester of aminoglycan at 300 times. Treatment 4 was designed with 6% oligosaccharide-combined with protein at a dilution of 1000 times (Beijing Green Agricultural Science and Technology Group Co., Ltd.) as recommended. Treatment 5 was water control. The treatment was applied as leaf spray every 7 days. The incidence was investigated after three applications. The disease index was recorded to distinguish the effect of treatment as shown in Table 4.

The classification of disease index:
Level 0: symptom free in the whole plant;
Level 1: Number of scabs is less than 2;
Level 3: Number of scabs is 3-5;
Level 5: Number of scabs is 6-8;
Level 7: Number of scabs is more than 9;
Level 9: The scabs are densely covered, and leaves are severely withered.

Disease index=Σ(quantity of leaves at every level×
relative level value)/(total quantity of leaves×
9)×100%

Control effect (%)=(disease index in control−disease
index in treatment)/disease index in control×
100%.

TABLE 4

Effect of ester of aminoglycan on prevention and control of virus diseases in *Capsicum annuum*

| Treatment | Disease index | Control effect (%) |
|---|---|---|
| Ester of aminoglycan diluted 1000 times | 3.65 | 81.16 |
| Ester of aminoglycan diluted 500 times | 2.25 | 88.38 |
| Ester of aminoglycan diluted 300 times | 1.74 | 91.02 |
| oligosaccharides-protein diluted 1000 times | 5.21 | 73.10 |
| water control | 19.37 | — |

The water control plants were seriously infected by disease. The control effect by the ester of aminoglycan obtained in Example 1 was significant in control of the disease as the symptom of mosaic virus in young leaves significantly reduced. The effect was significantly improved when the ester of aminoglycan concentration was increased from a dilution of 1000 times to 500 or 300 times.

Overall, it is clear from the results shown in the above tests that the preparation containing ester of aminoglycan in the present invention can effectively enhance the immune resistance in human and in animals, prevent and control illness in human and in animals that are caused by viruses or bacteria, and prevent plant diseases as well.

The invention claimed is:
1. An ester of aminoglycan, wherein the ester of aminoglycan comprises at least one of the following structural units:

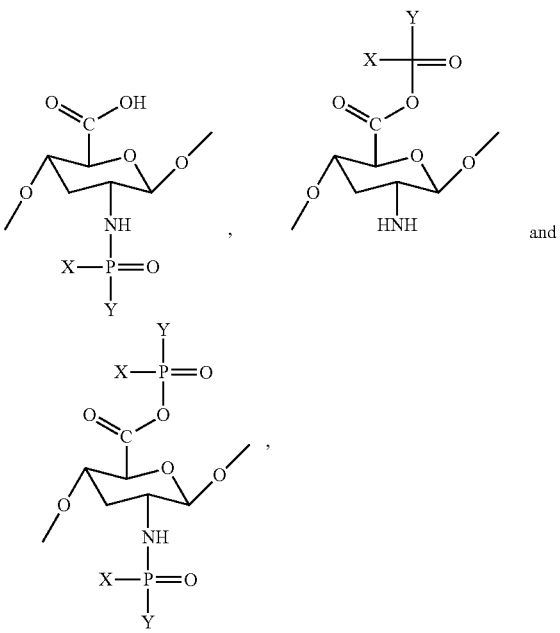

where X is —OH, —O—CH$_2$—CH$_2$—N—(CH$_3$)$_3$, —O—CH$_2$—CH$_2$—NH$_2$, metal element or non-metal element independently; and Y is —OH,

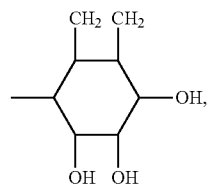

metal element or non-metal element independently.

2. A method of enhancing the immune resistance in human and animals, treating diseases in human and in animals caused by viruses or bacteria, strengthening the anti-stress ability of animals, improving the appetite of animals, promoting the growth of animals, inhibiting the growth of tumor, reducing blood lipid level and preventing and controlling viral diseases of plants comprising administering the ester of aminoglycan in claim 1 to a human, animal, or plant in need thereof.

3. The method according to claim 2, wherein the diseases in human or in animals comprise diseases harmful to human health, diseases caused by viruses, diseases caused by influenza virus, diseases caused by hepatitis A virus, diseases caused by hepatitis B virus, diseases caused by hepatitis C virus, diseases caused by HIV, diseases caused by herpes virus; cancerous diseases; diseases harmful to animals, viral and bacterial diseases harmful to livestock, poultry, aquatic product of fish, shrimp and crab, avian influenza, swine influenza, picornvirus disease, saprolegniasis, and streptococcusis.

\* \* \* \* \*